United States Patent [19]

Chen et al.

[11] Patent Number: 5,576,355
[45] Date of Patent: Nov. 19, 1996

[54] DIAMONDOID DERIVATIVES FOR PHARMACEUTICAL USE

[75] Inventors: Catherine S. H. Chen, Berkeley Hts., N.J.; Dong-ming Shen, Langhorne, Pa.

[73] Assignee: Mobil Oil Corp., Fairfax, Va.

[21] Appl. No.: 167,681

[22] Filed: Dec. 15, 1993

Related U.S. Application Data

[63] Continuation-in-part of Ser. No. 71,382, Jun. 4, 1993, Pat. No. 5,380,947.

[51] Int. Cl.$^6$ .................. A61K 31/14; A61K 31/045; A61K 31/12; A61K 31/195
[52] U.S. Cl. .................. 514/729; 514/461; 514/561; 514/642; 514/661; 514/662; 514/691; 549/341; 562/498; 562/499; 564/281; 564/459; 568/368; 568/373; 568/817; 568/818
[58] Field of Search .................. 514/729, 691, 514/642, 661, 662, 561, 461; 568/817, 818, 368, 373; 564/281, 459; 562/498, 499; 549/341

[56] References Cited

U.S. PATENT DOCUMENTS

| | | | |
|---|---|---|---|
| 3,152,180 | 10/1964 | Haaf | 260/561 |
| 3,257,456 | 6/1966 | Smith | 260/586 |
| 3,342,863 | 9/1967 | Hermann | 260/563 |
| 3,352,912 | 11/1967 | Prichard | 260/563 |
| 3,356,741 | 12/1967 | Schneider | 260/617 |
| 3,450,761 | 6/1969 | Schneider | 260/563 |
| 4,724,232 | 2/1988 | Rideout et al. | 514/50 |
| 4,956,481 | 9/1990 | Gillaspey et al. | 549/459 |
| 5,019,660 | 5/1991 | Chapman et al. | 585/22 |
| 5,053,434 | 10/1991 | Chapman et al. | 521/52 |
| 5,132,400 | 7/1992 | Gammill et al. | 530/317 |
| 5,194,538 | 3/1993 | Paskas et al. | 526/206 |
| 5,221,693 | 6/1993 | Shetty | 514/635 |

FOREIGN PATENT DOCUMENTS

| | | |
|---|---|---|
| 3921062AL | 3/1991 | Germany. |
| 1063365 | 3/1967 | United Kingdom. |

OTHER PUBLICATIONS

Raymond C. Fort, Jr., *Adamantane, The Chemistry of Diamond Molecules*, Marcel Dekker, Inc., New York 1976, pp. 1–5, 58–59, 66–111, 120–141, 156–159, 190–231.

George A. Olah, *Cage Hydrocarbons*, John Wiley & Son, Inc., New York 1990, pp. 39–47, 146–149, 174.

Vodicka et al. "Characterization of Oxygen–Containing Adamantane Derivatives, etc." *J. of Chromatography*, 366 (1986) 382–384.

Merson, et al., "Aids, The Unanswered Questions", Science 260, 1209–1396 (1993).

Kratsutskii, et al., Chemical Abstracts 104: 130230b (1986) "Amino Acids of the Adamantane Series. I Synthesis and Antiviral Activity of Adamantane α–Amino Acids And Their Derivatives", Khim.–Farm. Zh. 19 (7), 825–9 (1985).

Larder, et al., "HIV With Reduced Sensitivity to Zidovudine (AZT) Isolated During Prolonged Therapy", Science 243:1731–1734 (1989).

Montefiori, et al., "Evaluation of Antiral Drugs and Neutralizing Antibodies to Human Immunodeficiency Virus by a Rapid and Sensitive Microtiter Infection Assay", J. Clin. Microbiol 26:231–235 (1988).

Pauwels, et al., "Rapid and Automated Tetrazolium–Based Colorimetric Assay For the Detection of Anti–HIV Compounds", J. Virol Meth. 20:309–321 (1988).

Carmichael, et al., "Evaluation of a Tetrazolium–Based Semiautomated Colorimetric Assay: Assessment of Chemosensitivity Testing", Cancer Research 47:936–942. (1987).

Tada, et al., "An Improved Colorimetric Assay For Interleukin 2", J. Immunol. Meth. 93:157–165 (1986).

Harada, et al., "Infection of HTLV–III/LAV in HTLV–I–Carrying Cells MT–2 and MT–4 and Application in a Plaque Assay", Science 229: 563–566 (1985).

R. C. Fort, Jr., *Adamantane, The Chemistry of Diamond Molecules*, Marcel Dekker, New York 1976, pp. 327–357.

*Primary Examiner*—Peter O'Sullivan
*Attorney, Agent, or Firm*—Alexander J. McKillop; Dennis P. Santini

[57] ABSTRACT

A method of inhibiting viruses in which a virus is contacted with diamondoid alcohol, ketone, ketone derivative, adamantyl amino acid, quaternary salt or combinations thereof which have antiviral properties. These diamondoid derivatives are shown to have antiviral activity against HIV.

13 Claims, 5 Drawing Sheets

DIAMONDOID DERIVATIVES FOR PHARMACEUTICAL USE

CROSS-REFERENCE TO RELATED APPLICATION

This is a continuation-in-part of application Ser. No. 08/071,382 filed Jun. 4, 1993, now U.S. Pat. No. 5,380,947.

FIELD OF THE INVENTION

This invention relates to adamantane and diadamantane derivatives useful as pharmacological agents for use in pharmaceutical compositions such as antivirals.

BACKGROUND OF THE INVENTION

Numerous adamantane-based compounds have been tested for their activity against a number of infectious agents such as bacteria, viruses and as treatments against cancer and parkinson's disease, as well as a means of treating cardiac, circulatory and vascular disease, hypertension, depression and drug-induced extrapyramidal reactions. For a review on this topic, see Chapter 7 in *Adamantane, The Chemistry of Diamond Molecules*, R. C. Fort, Jr., Marcel Dekker, Inc., 1976.

Adamantane, also known as tricyclo-[3.3.1.1$^{3,7}$] decane, is a polycyclic alkane with the structure of three fused cyclohexane rings. The ten carbon atoms which define the framework structure are arranged in an essentially strainless manner thereby giving a very stable backbone for the addition of a variety of moieties. Four of these carbon atoms, the bridgehead carbons, are tetrahedrally disposed about the center of the molecule. The other six (methylene carbons) are octahedrally disposed. Because of the particular reactivity of adamantane, functional groups have been readily introduced at the bridgehead 1-, 3-, 5-, 7- positions of adamantane. U.S. Pat. Nos. 5,019,660 to Chapman and Whitehurst and 5,053,434 to Chapman teach diamondoid compounds which bond through the methylene positions of various diamondoid compounds. For a survey of the chemistry of diamondoid molecules, see *Adamantane, The Chemistry of Diamond Molecules*, Raymond C. Fort, Marcel Dekker, New York, 1976. For synthesis methods for adamantanes, see Paul Schleyer, *Cage Hydrocarbons*, George A. Olah, ed., Wiley, New York, 1990.

The IUPAC numbering system for adamantane and diadamantane are shown below.

ADAMANTANE 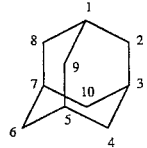

DIAMANTANE 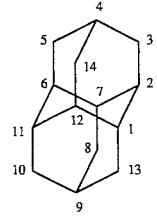

These have been called diamondoid compounds because their structures are part of the diamond lattice.

Certain derivatives of adamantane particularly those with amino substitutions at the (1-) position have been found to demonstrate activity against influenza and herpes, as well as against certain cancers such as angiocarcinoma and pancreatic carcinoma.

U.S. Pat. No. 3,152,180 to Haaf discloses N-tertiary alkyl amines and amides as intermediates for pharmaceutical use. For example, N-(adamantyl-1)-formamide is disclosed.

U.S. Pat. No. 3,342,863 to Hermann discloses certain lower alkyl 1-amino adamantane oxides having the formula

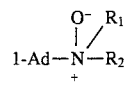

where $R_1$ and $R_2$ may be $C_{1-12}$ alkyl, as useful antiviral agents and antioxidants.

U.S. Pat. No. 3,352,912 to Prichard discloses (1-) substituted adamantane ($C_{10}$) derivatives having an aminomethyl or N-substituted aminomethyl group attached to a bridgehead (1-) nuclear carbon atom of adamantane and also (3-) substituted tricyclo [4.3.1.1$^{3,8}$] undecanes ($C_{11}$). The compounds are used as antiviral agents.

British Patent No. 1,063,365 describes adamantane substituted at the (1-) position with a primary or secondary amino group for use against swine influenza.

Chemical Abstracts 104:130230b (1986) lists an Abstract of a Russian article by P. A. Krasutskii et al., "Amino Acids of the Adamantane Series I. Synthesis and Antiviral Activity of Adamantane α Amino Acids and their Derivatives", Khim.-Farm. Zh 19(7):825–9 (1985) describing adamantane substituted at the (1-), (3-), (5-) and (7-) positions with hydrogen, methyl, or $(CH_2)_n CH(NH_2)CO_2H$ and having the formula

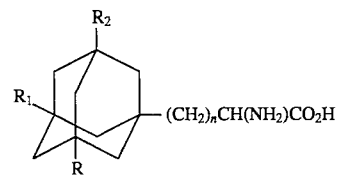

n = 0, 1
R, $R_1$ = H, Me
$R_2$ = H, Me, $CH(NH_2)CO_2H$

The products were tested using A— and Sindbis—type viruses. The results are not described in the English Abstract.

More recently, U.S. Pat. No. 5,221,693 to Shetty discloses bis-adamantane based compounds of the formulas

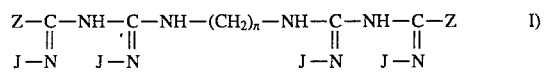

or

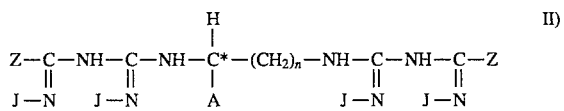

in which Z is an adamantane group. All of the compounds require two separate 1-adamantanyl moieties. The compounds are described as having antimicrobial and antiviral uses including against gram-positive and gram-negative bacteria, fungi, yeasts and enveloped viruses such as herpes and retroviruses.

A survey of adamantane compounds which have been tested for pharmacological activity is presented in *Adamantane, The Chemistry of Diamond Molecules*, Raymond C. Fort, Jr., Marcel Dekker, New York, 1976. Described compounds are adamantanes which are generally amino-substituted at the 1 or 2 position. The 1-aminoadamantanes which include primary and secondary amino functional groups were effective against certain viruses, such as influenza A, B, rous sarcoma, esh sarcoma, sendai, Newcastle, herpes, vaccinia and parainfluenza viruses. The survey discloses that adamantane which was amino-substituted with NHCSNHR at the (2-) position was modestly effective against herpes, vaccinia and Newcastle virus. 3R-Homoadamantane, R=CH$_2$NH$_2$, CH(CH$_3$)NH$_2$ or C(CH$_3$)$_2$NH$_2$, had activities similar to 1-aminoadamantane. However, 1-aminoadamantanes which were also substituted at the (3-) position with R=CO$_2$H or NH$_2$ showed no activity; R=OH showed slight activity. 3-CO$_2$H-1-AdCH$_2$NR$_2$ also showed no antiviral activity. While 3-R-1-AdNH$_2$, R=CH$_3$ or Br showed significant activity.

It is apparent from this survey that antiviral activities of adamantane have derived primarily from certain amino substitutions at the 1 or 2 positions of adamantane or 3-substituted homoadamantanes. It also appears that only analogues with amino substitutions at the (1-) position gave predictable activity.

German Patent DE 3921062 describes using 1-adamantamine hydrochloride in combination with AZT for therapy and prophylaxis of retroviruses such as HIV-1.

In the design of antiviral agents, viruses are targeted at steps in their life cycles. Attempts have been made to interrupt replication of viral nucleic acids in the infected cell or to interrupt the synthesis of viral proteins. However, viral multiplication must be inhibited without the undesirable side effect of damaging the host cells (cytopathic effect). The majority of anti-retrovirals and antivirals have been analogs of deoxyribonucleosides such as AZT, ddI and ddC which are used for HIV infections and which interfere with the synthesis of viral nucleic acids.

Amantadine at higher concentration (>0.5 mM), non-specifically inhibits viral entry into the cell by altering the pH of the endocytic vesicle. At lower concentration (about 5 μM), amantadine exhibits a selective strain-specific inhibition of virus assembly (See, e.g., Hay, A. J. and Zambon, M. C., "Multiple Actions of Amantadine Against Influenza Viruses", in Dev. Mol. Virol. 1984, 4 (Antiviral Drugs and Interferon: The Molecular Basis of Their Activity), Becker, Y., ed., 1984, 301–15. 1-Aminoadamantane hydrochloride (amantadine hydrochloride) is available commercially as an antiviral under the name Symmetrel and is used in the treatment and prevention of influenza A infections. The (1-) position of adamantane has also been substituted with —CH(CH$_3$)NH$_2$. The resulting compound is available commercially under the name Rimantadine which is also used in the treatment and prevention of influenza A.

Presently a great deal of research is focused on finding active agents against HIV infection. These agents are also usually targeted at a specific step in the complex life cycle of the virus. By interrupting a specific step in viral replication using therapeutic drugs, it is hoped that symptoms from infection can be at least delayed if not prevented. Most clinical successes to date have focused on the point in the viral life cycle where the genetic material of HIV (RNA) is reverse transcribed into DNA, which then infiltrates the host cell's genes. The drugs AZT, ddI and ddC work in this manner. Other methods for halting the life cycle target the HIV enzyme protease, which is required for assembling newly made HIV particles, or other proteins which govern replication.

Thus far the most effective compounds which have been approved to treat HIV infection act at the reverse transcription step. Presently, there is a need to find therapeutic agents which act at different stages of the viral life cycle. It is hoped that a combination of drugs acting at different steps of the viral life cycle would overcome the development of resistance by the virus. This type of combination drug therapy has been used successfully against intractable bacterial infections such as tuberculosis.

Compounds of the present invention have been found to act at more than one step, that is, either early in the life cycle, or in the later stages of the virus life cycle. These compounds also differ from previously used antiviral amantadine derivatives in that the new compounds have different substituted sites and different substituents at these sites in their structures. Particularly effective compounds in the present invention are diamondoid ketones. Previously, this class of compounds has not been known to have any pharmacological activity whatsoever.

It is an object of the invention to provide a method of inhibiting viruses using new diamondoid compounds.

It is a further object of the invention to provide effective diamondoid antiviral compounds useful in pharmaceutical formulations and in kits.

It is yet another object of the invention to provide diamondoid antiviral compounds effective in treating HIV infections.

It is another object of the invention to provide a method for treating viral infections.

It is still another object to provide an antiviral for use on drinking cups, syringes and specimen containers, birth control devices such as condoms, etc. e.g., as a coating or as an additive, for example, in blood product preparations and similar biologicals.

SUMMARY OF THE INVENTION

Accordingly, the invention provides a method of inhibiting a virus which comprises contacting with a compound of formula I or II or combination thereof. Compounds of formula I are as follows:

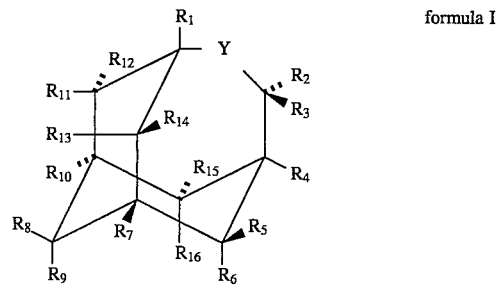

formula I wherein

Y is a bond, CH$_2$, oxygen, sulfur, sulfoxide, sulfone or NH;

R$_1$, R$_4$, R$_7$ and R$_{10}$ are individually hydrogen, hydroxyl, lower alkyl of one to eight carbon atoms, OZ where Z is lower alkyl of 1 to 8 carbons, COQ where Q is hydrogen or lower alkyl of 1 to 8 carbons or OSO$_3$H; preferably, hydroxyl, methyl or hydrogen. These are the bridgehead positions.

R$_2$, R$_3$, R$_5$, R$_6$, R$_8$, R$_9$, R$_{11}$, R$_{12}$, R$_{13}$, R$_{14}$, R$_{15}$ and R$_{16}$ are individually hydrogen, hydroxyl, lower alkyl of 1 to 8 carbons, double-bonded oxygen, COQ where Q is hydrogen or lower alkyl of 1 to 8 carbons, OCOQ' where Q' is hydrogen, lower alkyl of 1 to carbons or aryl; OSO$_3$H,

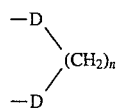

where n is 2 or 3 and D is oxygen or sulfur, carboxy, COOQ where Q is hydrogen or lower alkyl of 1 to 8 carbons, $(OZ)_2$ where Z is lower alkyl of 1 to 8 carbons, =N-Z' where Z' is hydrogen, $NH_2$, OH,

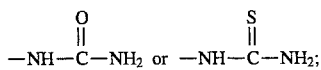

NHQ" where Q" is lower alkyl of 1 to 5 carbons, SH, an amino acid, or a secondary or tertiary amine of the formula

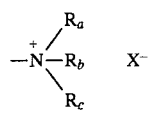     formula A wherein $R_a$ is hydrogen or lower alkyl of 1 to 8 carbons; preferably methyl;

$R_b$ is lower alkyl of 1 to 8 carbons; preferably methyl;

$R_c$ is hydrogen or lower alkyl of 1 to 8 carbons; preferably methyl;

$X^-$ is a counterion such as halogen, hydroxide, sulfate, nitrate, phosphate or other anion.

These are non-bridgehead positions and the substituents for these positions, particularly for $R_2$ or $R_3$, are preferably double bonded oxygen,

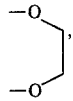

an amino acid, a moiety of formula A or hydrogen. $R_1$–$R_{16}$ are not all hydrogen.

Compounds of formula II are as follows:

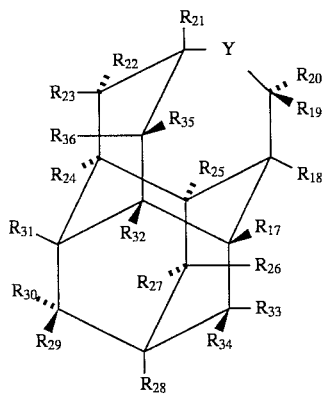     formula II wherein

Y is a bond, $CH_2$, oxygen, sulfur, sulfoxide, sulfone or $R_{17}$, $R_{18}$, $R_{21}$, $R_{24}$, $R_{25}$, $R_{28}$, $R_{31}$ and $R_{32}$ are individually hydrogen, hydroxyl, lower alkyl of 1 to 8 carbons, OZ, where Z is lower alkyl of 1 to 8 carbons, COO where Q is hydrogen or lower alkyl of 1 to 8 carbons, $OSO_3H$, $NH_2$, HHR', NR'R", $\overset{+}{N}R'R"R'''$,

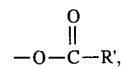

where R',R" and R'" are individually lower alkyl of 1 to 8 carbons, SH, aryl such as phenyl, phenyl substituted with halogen or phenyl substituted with lower alkyl of 1 to 8 carbons, furyl or pyridyl. These are bridgehead positions. The R's for these bridgehead positions are preferably hydroxyl or amino groups.

$R_{19}$, $R_{20}$, $R_{22}$, $R_{23}$, $R_{26}$, $R_{27}$, $R_{29}$, $R_{30}$, $R_{33}$, $R_{34}$, $R_{35}$ and $R_{36}$ are individually hydrogen, hydroxyl, double-bonded oxygen, COQ where Q is hydrogen or lower alkyl of 1 to 8 carbons, OCOQ' where Q' is hydrogen, lower alkyl of 1 to 8 carbons or aryl; $OSO_3H$,

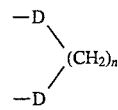

where n is 2 or 3 and D is oxygen or sulfur, COOQ where Q is hydrogen or lower alkyl of 1 to 8 carbons, $(OZ)_2$ wherein Z is a lower alkyl with 1 to 8 carbons, =NZ' wherein Z' is hydrogen, $NH_2$, OH,

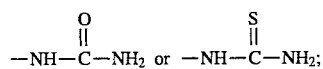

$NH_2$, NHR', NR'R" where R' and R" are individually lower alkyl of 1 to 8 carbons; SH, an amino acid or a moiety having the formula

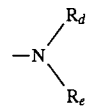     formula B or

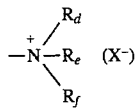     formula C wherein $R_d$ is hydrogen or lower alkyl of 1 to 8 carbons, preferably methyl;

$R_e$ is $(CH_2)_n \overset{+}{N}R'R"R'''(CH_3)_3$ $(X^-)$, n=2 or 3, or lower alkyl with 1 to 8 carbons;

$R_f$ is lower alkyl of 1 to 8 carbons, preferably methyl;

X is a counterion such as halogen, hydroxide, sulfate, nitrate, phosphate, hydrogen phosphate or other anion.

$R_{17-36}$ are not all hydrogen. These are the non-bridgehead positions and the preferred substituent for one of these positions is double-bonded oxygen, formula B or formula C.

The various alkyl groups described in formula I and formula II may be branched or unbranched, and typical examples include methyl, ethyl, n-propyl, iso-propyl, n-butyl, sec-butyl, tert-butyl, isobutyl, pentyl, hexyl, heptyl and octyl.

Aryl groups are typically phenyl but also may be other aryl groups, for example, naphthyl, pyrrolyl, furanyl, thiophenyl, pyridyl, etc. The aryl group may be further substituted, e.g. by an inorganic such as halo, or an organic such as an alkyl group of 1 to 8 carbons.

As used herein, the term "individually" means each radical in a grouped set of radicals can be the same or different. All substituents contribute to a stable molecule so that, e.g., $R_2$ and $R_3$ cannot both be double bonded oxygen.

As used herein diamondoid means adamantane or diamantane.

The compounds of formula I and formula II are used to inhibit activity or virus entry into cells or replication of a virus by contacting an effective antiviral amount of the compound with a virus, a virus-infected cell or virus-infectable cell so that a virus-caused cytopathic effect or viral replication is avoided.

The compounds of formula I and formula II have antiinfective activity and they may be used for the preparation of pharmaceutical formulations and in kits.

The invention is effective in inhibiting retroviruses including lentiviruses and the oncoviridae. The invention is particularly effective against human retrovirus of the Lentiviral family, Human Immunodeficiency Virus (HIV).

Advantageously, antiviral activity has been shown at more than one stage of the viral life cycle; and antiviral activity has been shown against an AZT resistant strain of HIV as well as against a primary clinical isolate of the virus.

DETAILED DESCRIPTION OF THE INVENTION

Figure 1:
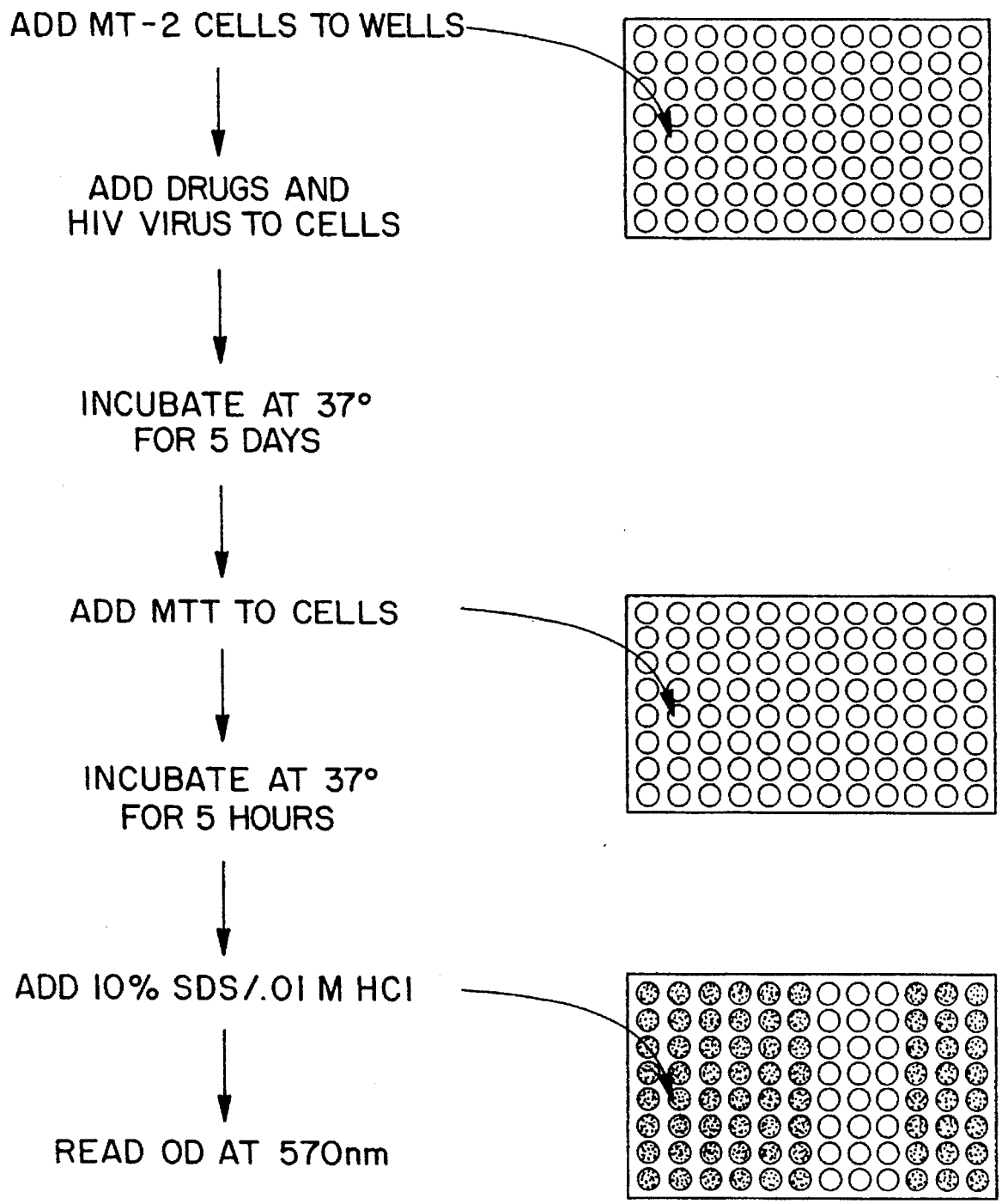
FIG. 1 is a protocol for an MTT reduction antiviral assay.
Figure 2A:
FIG. 2A–F are photographs illustating syncytia inhibition against HIV-1/MN virus strain.
Figure 2B:
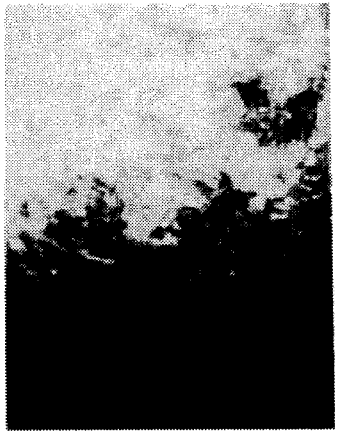
Figure 2C:
Figure 2D:
Figure 2E:
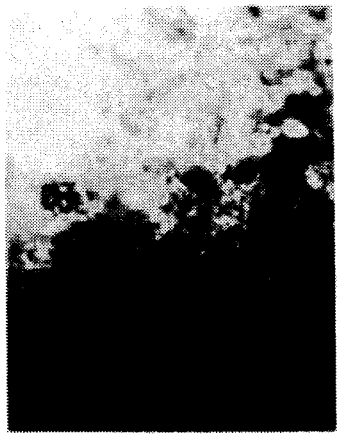
Figure 2F:
Figure 3A:
FIG. 3A–F are photographs illustrating syncytia inhibition against HIV-1/AZTR and VP6 virus strains.
Figure 3B:
Figure 3C:
Figure 3D:
Figure 3E:
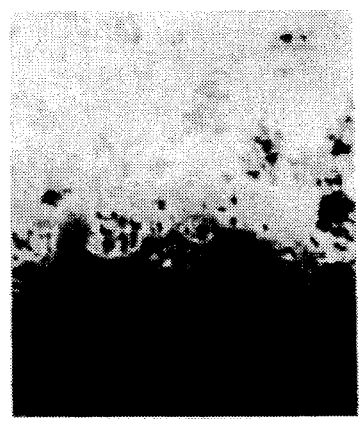
Figure 3F:
Figure 4A:
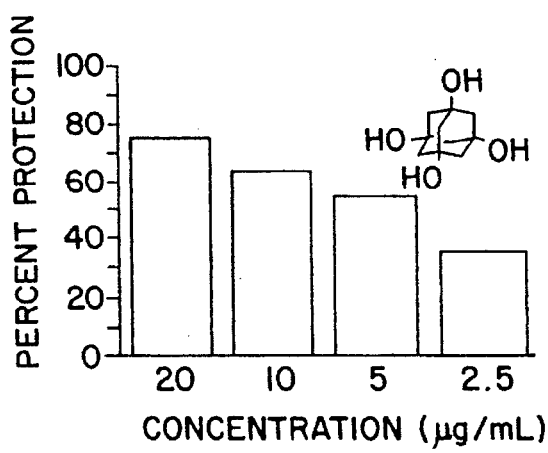
FIG. 4A–H shows graphical representations of inhibition of HIV-1/MN induced CPE by the compounds of the invention.
Figure 4B:
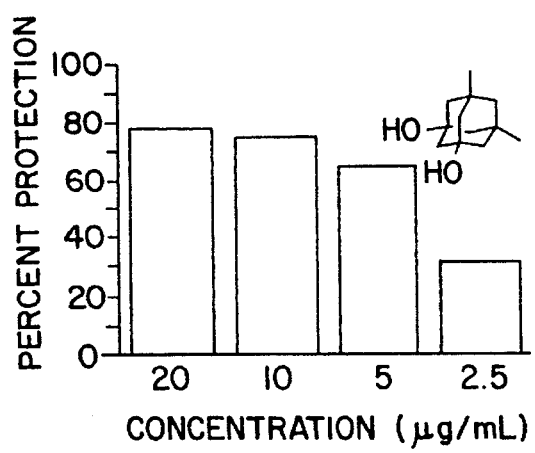
Figure 4C:
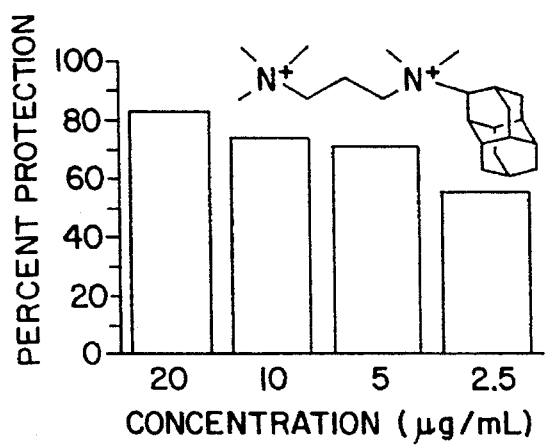
Figure 4D:
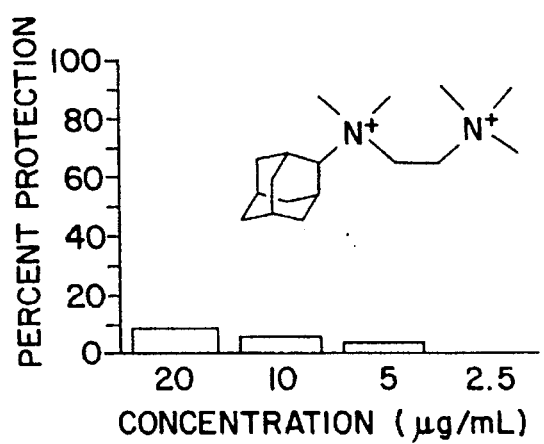
Figure 4E:
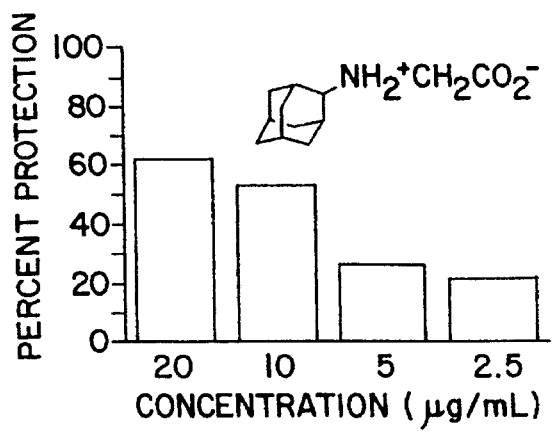
Figure 4F:
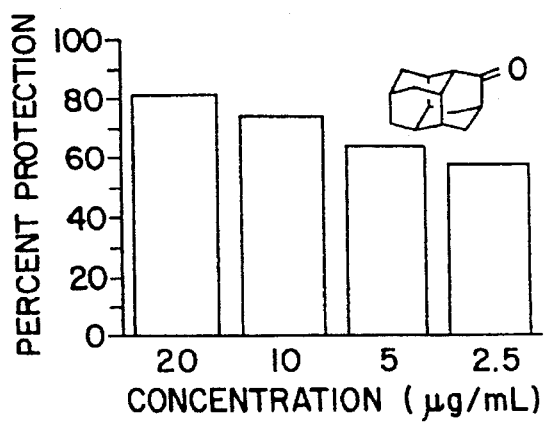
Figure 4G:
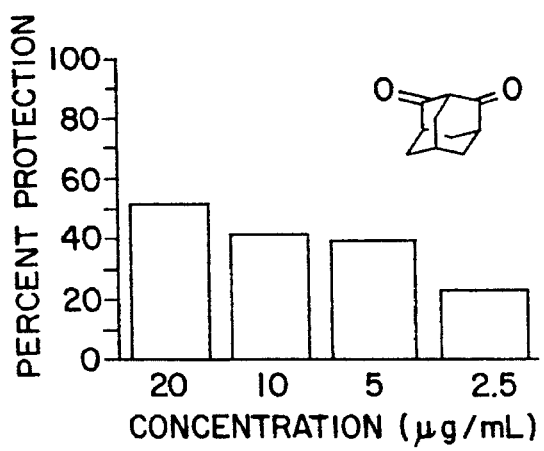
Figure 4H:
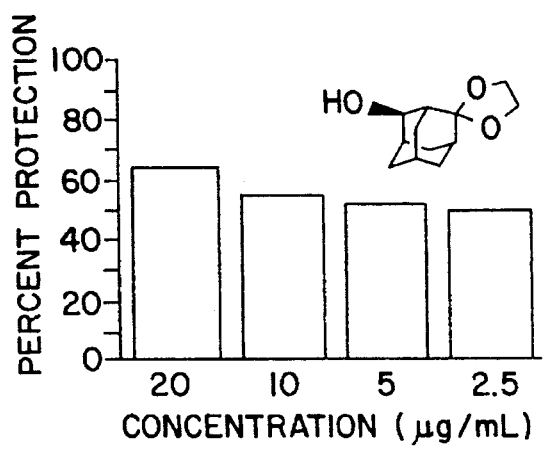

Compounds useful herein are described for formulas I and II above. Examples of compounds having formula I are hydroxy diamondoids, i.e., diamandoid alcohols or diamondoid polyols, diamondoid quaternary ammonium compounds, diamondoid ketones and their carbonyl derivatives, and diamondoid amino acids, for example:

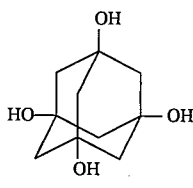

$C_{10}H_{16}O_4$ 1,3,5,7-adamantanetetraol
(1,3,5,7-tetrahydroxytricyclo
[3.3.1.1$^{3,7}$]decane)

and

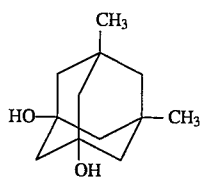

$C_{12}H_{20}O_2$ 1,3-dihydroxy-5,7-dimethyladamantane
(1,3-dihydroxy-5,7-dimethyl)
tricyclo [3.3.1.1$^{3,7}$] decane
(1,3-Adamantanediol-5,7-dimethyl)
(5,7-dimethyl-1,3-adamantanediol).

The compounds of the invention also include 2-adamantyl amino acids such as

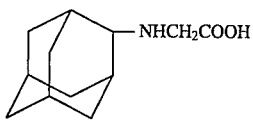

$C_{12}H_{19}NO_2$

N-2-adamantyl glycine
(N-2-adamantylamino)
acetic acid and diamondoid ketones such as

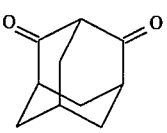

$C_{10}H_{12}O_2$ 2,4-adamantanedione
(tricyclo[3.3.1.1$^{3,7}$]decane-2,
4-dione)

and carbonyl derivatives of diamondoid ketones such as

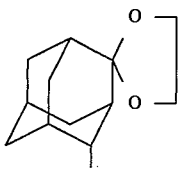

$C_{12}H_{18}O_3$

4(e)-hydroxy-2-adamantanone
ethylene glycol ketal
(Spiro[1,3-dioxolane-2,2'-
tricyclo [3.3.1.1$^{3,7}$] decane-
4'-ol, 1'α,3'β,4'α,5'α,7β

Examples of compounds having formula II are

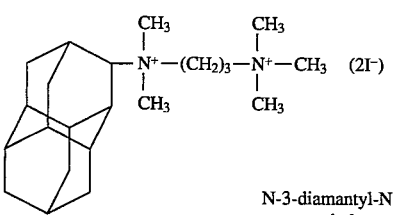

$C_{22}H_{40}N_2I_2$

N-3-diamantyl-N,N,N',N',N'-
pentamethyl propane 1,3-
bis ammonium diiodide and

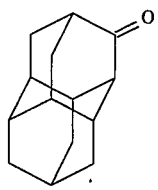

$C_{14}H_{18}O$ 3-diamantanone
(octahydro-3,5,1,7-
[1.2.3.4]butanetetrayl
naphthalene-2(1H)-one Preferred compounds are diamondoid ketones.

The invention also relates to the use of the compounds of formula I and formula II and their pharmaceutically acceptable salts when appropriate for the preparation of pharmaceutical formulations. The salts may be prepared using simple acid-base reactions.

The pharmaceutical composition may be administered in any number of acceptable and physiologically tolerable ways such as orally, subcutaneously, percutaneously, intramuscularly, by suppository, intravenously, intranasally (inhaled), or intraarticularly or by external application including nebulization (spraying).

The pharmaceutical compositions can be formulated and prepared by established pharmaceutical procedures into composition for administration. The compounds may be employed in admixture with conventional excipients, i.e., pharmaceutically acceptable organic or inorganic carriers which do not deleteriously interact with the active compounds.

The compounds of this invention possess valuable pharmacological properties for both human and veterinary medicine. The compounds display antiviral and antitumor effects and are useful particularly in the prevention and chemoprophylaxis of viral illnesses. The compounds are also useful in the treatment of bacterial and mycotic infections. These compounds are particularly useful as antivirals.

In addition, the compounds can be used in in vitro diagnostics (e.g., in an assay for renin, bacteria, virus, etc.).

They can be employed in admixture with carriers, germicides, fungicides, soaps, and in spermicides and on condoms and birth control devices, etc. and used in antiseptic solutions and the like, particularly in conjunction with hospital housekeeping procedures, e.g., to combat HIV. The compounds can be applied on syringes/needles, containers such as specimen containers, gowns, gloves, etc., and in biologicals and in blood products such as clotting factors for clinical use.

The compounds of the invention are also useful as intermediates to synthesize other pharmaceuticals such as functionalized triamines, tetraamines, and higher functionalized diamendoid-containing amines and their derivatives.

A kit for use in determining the presence of virus, particularly retrovirus and more particularly, Human Immunodeficiency Virus (HIV) or Human T-cell Leukemia Virus (HTLV), which are implicated in Acquired Immunodeficiency Syndrome (AIDS), includes a compound of formula I or formula II or combinations thereof. The virus causes cells grown in tissue culture to demonstrate a cytopathic effect and to form syncytia. A syncytium is a multinucleated cell formed by cytoplasmic fusion, without nuclear fusion, of a number of individual cells. Various dye uptake tests, immunoassays and reverse transcriptase assay can also be used to test for virus. Therefore, the compounds of formula I and formula II can be used in a microtiter infection assay by screening for a known viral effect such as the formation of syncytia or, e.g., using a dye uptake test.

The pharmacological compounds of this invention are generally administered to animals, including mammals, fish, reptiles, and avians, more preferably to mammals including humans, primates, livestock, cattle, horses, household pets including cats and dogs; and avians including poultry.

The pharmacologically active compounds of this invention can be processed in accordance with conventional methods of pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose, or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, merely to name a few. The pharmaceutical preparations can be sterilized and if desired mixed with auxiliary agents, e.g., lubricants, preservatives, stabilizers, wetting agents, emulsifier, salts for influencing osmotic pressure, buffers, coloring, flavoring, and/or aromatic substances and the like which do no deleteriously react with the active compounds. They can also be combined where desired with other agents, e.g. vitamins.

For parenteral application, particularly suitable are injectable, sterile solutions, preferably oily or aqueous solutions, as well as suspensions, emulsions, or implants including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed. Nebulizers and inhalation aerosols may also be used.

Sustained or directed release compositions can be formulated, e.g., liposomes or those wherein the active compound is protected with differentially degradable coating, e.g., by microencapsulation, multiple coatings, etc. It is also possible to freeze-dry the new compounds and use the lypophilizates obtained, for example, for the preparation of products for injection.

For topical application, there are employed as non-sprayable forms, viscous to semi-solid or solid forms comprising a carrier compatible with topical application and having a dynamic viscosity preferably greater than water. Suitable formulations include but are not limited to transdermal patches, solutions, suspensions, emulsions, creams, ointments, powders, liniments, salves, aerosols, etc., which are, if desired, sterilized or mixed with auxiliary agents, e.g., preservations, stabilizers, wetting agents, buffers, or salts for influencing osmotic pressure, etc. For topical application, also suitable are sprayable aerosol preparations wherein the active ingredient, preferably in combination with a solid or liquid inert carrier material, is packaged in a squeeze bottle or in admixture with pressurized volatile, normally gaseous propellant, e.g., a freon.

Generally the compounds of this invention are dispensed in unit dosage from comprising from 10 to 1000 mg in a pharmaceutically acceptable carrier per unit dosage. They are incorporated in topical formulations in concentrations from about 0.01 to about 3 weight percent.

The dosage of the compounds according to this invention generally is from about 0.1 to about 100 mg/kg day, preferably 0.1 to 20 mg/kg day when administered to patients, e.g., humans as an antiviral.

It will be appreciated that the actual preferred amounts of active compound in a specified case will vary according to the specific compound being utilized, the particular compositions formulated, the mode of the application, and the particular situs and organism being treated. Dosages for a given case can be determined using conventional considerations, e.g., by customary comparison of the differential activities of the subject compounds and of a known agent, e.g., by means of an appropriate conventional pharmacological protocol.

The treatment of viral disease has been approached by inhibiting adsorption or penetration of virus into the cells, inhibiting intracellular processes which lead to the synthesis of viral components, or inhibition of release of newly synthesized virus from the infected cell. The inhibition of one or more of these steps depends on the chemistry or mode of action of the virus.

Viruses share certain common characteristics: they consist of a nucleic acid genome surrounded by a protective protein shell (capsid) and the protein shell may be enclosed in an envelope which further includes a membrane. Viruses can multiply only inside living cells after the virus has infected the cell and the viral genome has been introduced into the cell. Animal viruses may differ in their types of nucleic acid which may be double-stranded DNA, single-stranded DNA, single-strand positive RNA, single-strand negative RNA, and double-stranded RNA.

Double-strand DNA viruses include Hepadna viruses such as the virus causing hepatitis B (Dane particle); Poxviridae such as the viruses causing smallpox (variola), swinepox, rabbit myxoma and orf; Herpesviridae such as the viruses causing herpes simplex (HSV-1 and HSV-2), cytomegaly, viral lymphoproliferative disease, Burkitt lymphoma, nasopharyngeal carcinoma in China, infectious mononucleosis (Epstein-barr) and chickenpox (varicella-zoster); and Adenoviridae such as adenovirus causing acute respiratory tract disease.

Single strand DNA viruses include Papoviridae which are non-enveloped viruses causing human warts (papillomavirus) and JC virus causing progressive multifocal leukoencephalopathy.

Positive-strand RNA viruses include Retroviridae such as the viruses causing human T-cell leukemia (HTLV-1 and HTLV-II) and Acquired Immunodeficiency Disease (AIDS) (HIV-1 and HIV-2). The HIV viruses have many characteristic of lentiviruses.

Positive-strand RNA viruses also include Picornaviridae such as the enteroviruses causing polio, Coxsackie virus infections and hepatitis A.

Negative-strand RNA viruses include Orthomyxoviridae such as the viruses causing influenza A, B and C; Paramyxoviridae such as the viruses causing mumps, measles, parainfluenza, and respiratory syncytial disease (pneumovirus); and Rhabdoviridae such as the virus causing rabies.

Double-strand RNA viruses include Reoviridae such as the viruses causing certain gastroenteritis (rotavirus).

More extensive discussion of viruses causing human disease can be found, e.g., in J. S. Specter et al., *Clinical Virology Manual*, Elsevier, N.Y., 1992.

The treatment of viral disease by chemical drugs has targeted inhibition of intracellular metabolic processes which lead to the synthesis of viral constituents or release of virus from the host cell (late); and inhibition of absorption or penetration of the virus into the host cell or integration of the viral genome into that of the host cell (early).

The invention is particularly concerned with pharmaceutical preparations which can be used in the treatment of HIV infection and AIDS. Current knowledge on HIV infection and AIDS is extensively discussed in "AIDS, The Unanswered Questions", Science, 260, 1209–1396 (May 1993).

Adamantane may be synthesized by aluminum halide—catalyzed rearrangement of polycyclic hydrocarbons (see, e.g., J. March, *Advanced Organic Chemistry, Reactions, Mechanisms and Structures*, John Wiley & Sons, New York 1985, pp. 961–962). U.S. Pat. Nos. 5,019,660 to Champman and Whitehurst, and 5,053,434 to Chapman also describe synthesis of diamandoid compounds which bond through the octahedrally disposed methylene carbons of diamandoid compounds.

Some compounds of the invention may be synthesized using the diquaternary ammonium salt synthesis method described in U.S. Pat. No. 5,256,391.

The following non-limiting examples illustrate the invention.

Compound Synthesis

1. Synthesis of 1,3,5,7-Tetrahydroxyadamantane

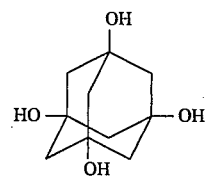

1,3,5,7-Tetrahydroxyadamantane was synthesized by oxidation of adamantane using methy(trifluoromethyl)dioxirane (References: Oxidation by Methyl(trifluomethyl)dioxirane. 2. Oxyfunctionalization of Saturated Hydrocarbons, Rossella Mello, Michele Fiorentino, Caterina Fusco, and Ruggero Curci, J. Am. Chem. Soc. 1989, 111, 6749; Oxidation by Methyl(trifluomethyl)dioxirane. 3. Selective Polyoxyfunctionalization of Adamantane, Rossella Mello, Luigi Cassidei, Michele Fiorentino, Caterina Fusco, and Ruggero Curci, Tetrahedron Lett., 1990, 31, 3067). In our synthesis, a one-pot oxidation procedure was developed. Methyl(trifluoromethyl)dioxirane was generated in situ from 1,1,1-trifluoro-2-propanone ($CF_3COCH_3$, hereafter TFP) and buffered (pH 7, $NaHCO_3$) aqueous potassium peroxomonosulfate ($KHSO_5$). The commercial product triple salt $2KHSO_5 \cdot KHSO_4 \cdot K_2SO_4$ (OXONE by DuPont) was used as a source of potassium peroxomonosulfate.

Into a 4-neck flask immersed in a cooling bath and equipped with a low temperature condenser (–20° C.), an air driven, well sealed mechanical stirrer, a solid addition funnel, and a thermocouple, were added 5.0 grams adamanatane (purified by recrystallization from heptane), 150 ml methylene chloride, 200 ml double distilled water, 192 grams sodium bicarbonate (pH 7 buffer), and 300 ml t-butanol. The mixture was stirred and cooled to 0° C. and 200 grams TFP were added. The temperature rose to 10° C. The mixture was stirred and cooled down to –8° C., 200 grams of OXONE were added from the solid addition funnel in the course of 3 hours. There was no rise in temperature during the OXONE addition. The reaction mixture was stirred at 0° C. overnight (16 hours). The TFP was recovered by distillation by heating the pot to 40° C. and condensing the TFP in a receiver immersed in Dry Ice/Acetone. The remainder paste-like mixture was filtered by suction with ease, and a clear colorless solution was obtained. The solution was rotavapped to dryness. The crude product by GC analysis contained 95% polyhydroxyadamantane products of which 5% was 1,3,5-trihydroxyadamantane and 95% was 1,3,5,7-tetrahydroxyadamantane. Pure 1,3,5,7-tetrahydroxyadamantane was obtained by recrystallizing the crude product from ethanol/methylene chloride. Calculated for $C_{10}H_{16}O_4$: C:59.98; H:8.06; 0:31.96. Found: C:59.75; H:8.23; 0:32.02.

Synthesis of 1,3-Dihydroxy-5,7-Dimethyladamantane

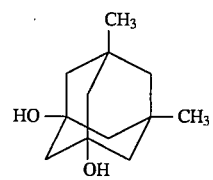

1,3-Dihydroxy-5,7-dimethyladamantane was synthesized in a similar manner as described for 1,3,5,7-tetrahydroadamantane. Into a 4-neck flask immersed in a cooling bath and equipped with a low-temperature condenser (–20° C.), an air-driven, well-sealed mechanical stirrer, a solid addition funnel, and a thermocouple, there were charged 4.5 grams, 1,3-dimethyladamantane (Aldrich, 99%+), 100 ml methylene chloride, 96 grams sodium bicarbonate, 100 ml double distilled water. Upon stirring and cooling the mixture to 0° C., 100 grams TFP were added and the temperature of the mixture went to 10° C. After the mixture was cooled down again to 0° C., 100 grams OXONE were added in the course of an hour. The reaction mixture was stirred at −5° C. for additional 20 hours (overnight). The TFP was recovered by distilling the reaction mixture at a pot temperature of 50° C. into a receiver immersed in DryIce/acetone. The remainder mixture was filtered by suction over Celite as a filter aid. The filtrate was yellow and contained two phases (aqueous and organic). It was rotavapped to dryness. The dry solid was extracted with ethanol and filtered. Crude product was obtained by evaporating off the ethanol which contained more than 95% 1,3-dihydroxy-5,7-dimethyladamantane. The brownish crude product was purified by crystallization from ethanol/methylene chloride mixture to a GC pure product with a molecular weight of 196 gram/mole (by GC-MS). Calculated for $C_{12}H_{20}O_2$:196.28 gram/mole 3. Synthesis of N-3-Diamantyl-N,N,N',N',N'-pentamethyl-1,3-Propane Bis-Quaternary Ammonium Diiodide

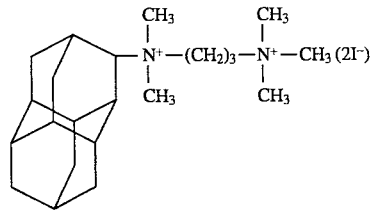

Starting Materials:

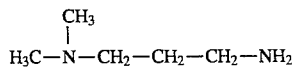

N, N-Dimethylproplylenediamine, 100%: 51.1 gm (0.5 mole) 3-Diamantanone, 97%: 101.2 gm (0.5 mole).

Solvent: Ethanol; 300 ml.

Catalyst for Hydrogenation: Pd (5 wt. %) on activated carbon, 16.0 gm.

The reactants were mixed in a 600 ml Parr reactor. The reactor was sealed and purged with nitrogen gas, then filled with $H_2$ for reductive amination. The $H_2$ pressure in the reactor was maintained at 500 psig and $H_2$ was continuously fed to the Parr reactor from a reservoir bomb. The reaction was carried out at 75° C. for 72 hours at which time no more $H_2$ was taken up. The product (formula 3A) was isolated in 100% yield (143.7 gm). The product (formula 3A) was methylated and 132 gm of product (formula 3B) was obtained in 84% yield based upon starting materials. The product (formula 3B) was quaternized with 61.9 gm $CH_3I$ at 45° C. or lower by adding the $CH_3I$ slowly to obtain a product having formula 3C in quantitative yield. The product formula 3C was then subjected to further quaternization in DMF with 93 gm additional $CH_3I$ in a 600 ml Parr reactor at 75° C. for 72 hours. The reactor was cooled down to ambient temperature and opened. The solid crystalline product was first washed with DMF, then with hot ethanol until the washer was clear (about 5 liters). The washed product was white and dried at 75° C./30 mm Hg to 240.2 gm (82% yield based upon starting materials). The initial DMF washing was rotavapped and the solid product was again washed with ethanol to give an additional 4.5 gm of the product formula 3D. The product of formula 3D was then recrystallized in boiling water and white glistening crystals were obtained from water at room temperature.

Elemental analysis of the product formula 3D: Calculated for $C_{22}H_{40}N_2I_2$: C: 45.06; H: 6.88; N: 4.78; I: 43.29. Found C: 44.99; H: 6.95; N: 4.72; I: 43.23.

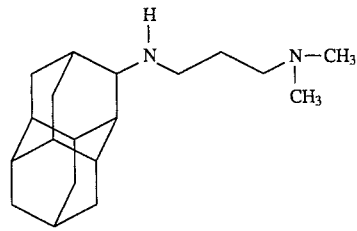

3A

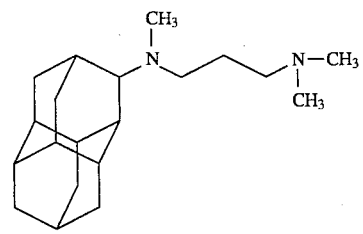

3B

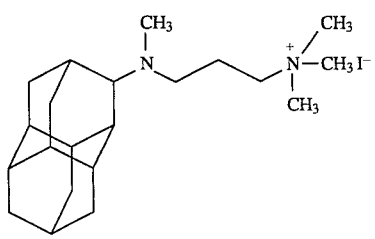

3C

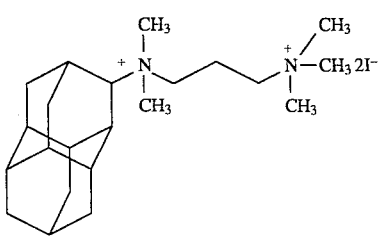

3D

4. Synthesis Of N-2-Adamantyl-N,N,N'N'N'-Pentamethyl-1,2-Ethane Diquaternary Ammonium Diiodide

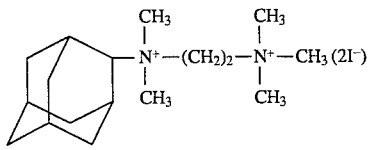

For the synthesis of

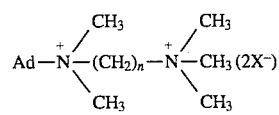

n = 2
Ad = 2-adamantyl

Starting Materials:

| | |
|---|---|
| CH₃—N(CH₃)—CH₂—CH₂—NH₂ | N,N,-Dimethylethylenediamine, 95%<br>111.4 gm (1.2 moles). |

2-adamantanone, 99%: 151.7 gm (1.0 mole).
Solvent: cyclohexane: 300 ml
Temperature: The pot temperature was kept at about 80° C. and water was azeotroped out at 69° C.

Products:

| Product | Yield, % | ¹³CNMR | Elemental Analysis |
|---|---|---|---|
| 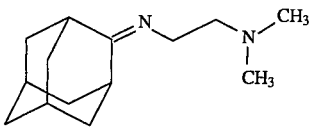 adamantylidene=N—CH₂—CH₂—N(CH₃)₂ | 100 | 180.7, 60.9, 48.3, 46.0, 43.9, 39.3, 38.5, 36.7, 33.4, 28.0 | — |
| 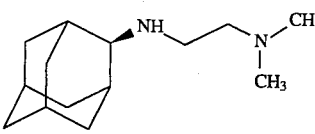 adamantyl—NH—CH₂—CH₂—N(CH₃)₂ | 100 | 62.3, 60.9, 48.3, 45.7, 38.2, 37.8, 32.3, 31.5, 28.0, 27.7 | — |
| 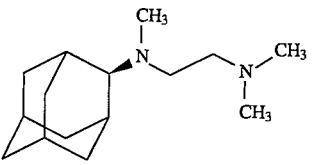 adamantyl—N(CH₃)—CH₂—CH₂—N(CH₃)₂ | 90 | 67.7, 56.6, 52.4, 46.4, 39.8, 38.2, 37.7, 31.7, 30.0, 27.8, 27.6 | — |
| 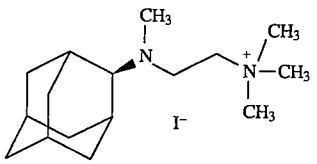 adamantyl—N(CH₃)—CH₂—CH₂—N⁺(CH₃)₃ I⁻ | 90 | 69.3, 63.3, 54.4, 48.5, 41.5, 40.2, 39.7, 33.5, 31.9, 29.2 (2 types) | Calculated for $C_{16}H_{31}N_2I$:<br>C: 50.79; H: 8.26; N: 7.40; I: 33.5<br>Found:<br>C: 51.13; H: 8.23; N: 7.38; I: 33.8 |
| 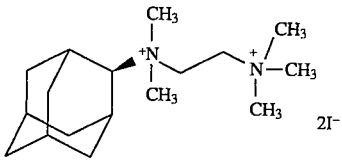 adamantyl—N⁺(CH₃)₂—CH₂—CH₂—N⁺(CH₃)₃ 2I⁻ | 86 | 83.0, 61.4, 59.7, 57.4, 54.5, 42.8, 39.9, 34.2, 31.7, 29.9, 28.7 | Calculated for $C_{17}H_{34}N_2I_2$:<br>C: 39.25; H: 6.59; N: 5.38; I: 48.79<br>Found:<br>C: 39.02; H: 6.40; N: 5.34; I: 48.23 |

*Yield based on 2-adamantanone

For the synthesis of the compound when n=3, the starting materials are

| | |
|---|---|
| CH₃—N(CH₃)—CH₂—CH₂—CH₂—NH₂ | N,N,-Dimethylethylenediamine, 95%<br>122.6 gm (1.2 moles). |

2-adamantanone, 99%: 151.7 gm (1.0 mole).
Solvent: cyclohexane: 300 ml
Temperature: The pot temperature was kept at about 80° C. and water was azeotroped out at 69° C.

Product:

| Product | Yield, % | ¹³CNMR | Elemental Analysis |
|---|---|---|---|
| 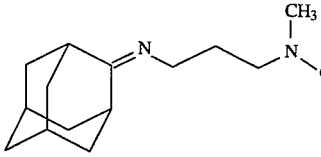 adamantylidene=N—CH₂CH₂CH₂—N(CH₃)₂ | 97 | 179.9, 581, 47.9, 45.7, 43.9, 39.3, 38.4, 36.6, 33.0, 29.5, 27.9 | — |

-continued

| Structure | Yield* | NMR | Analysis |
|---|---|---|---|
| 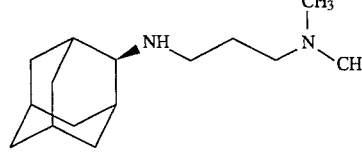 | 97 | 62.3, 58.8, 46.0, 45.9, 38.4, 38.0, 32.3, 31.6, 28.9, 28.1, 27.9 | — |
| 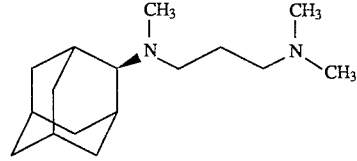 | 74 | 67.3, 58.7, 52.1, 46.0, 39.1, 38.2, 37.8, 31.7, 29.9, 27.8, 27.6, 23.7 | — |
| 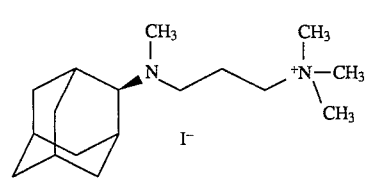 | 69 | 71.0, 68.8, 57.1, 53.4, 42.2, 40.9, 40.7, 34.3, 32.4, 30.4 (2 types of carbons), 20.8 | — |
| 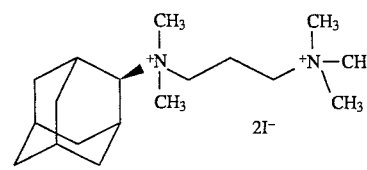 | 70 | 83.1, 66.6, 64.4, 57.4, 54.6, 43.4, 40.6, 34.7, 32.2, 30.5, 29.2, 21.0 | Calculated for $C_{18}H_{36}N_2I_2$: C: 40.46; H: 6.79; N: 5.24; I: 47 Found: C: 40.09; H: 6.89; N: 5.19; I: 48 |

*Yield based on 2-adamantanone.

Synthesis of N-2-Adamantyl Glycine

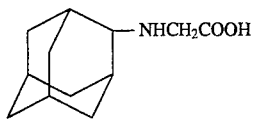

This compound was synthesized by reductive amination of 2-adamantanone with glycine. A 600 ml stainless steel Parr reactor, equipped with a stirrer, two inlets, one with a tubing reaching nearly to the bottom of the reactor, and an outlet was used. Into the open reactor there were charged 100 grams of glycine (Aldrich, 99+%), 206.7 grams of 2-adamantanone (Aldrich, 99%), 10 grams of palladium (5%) on charcoal, and 300 grams of glacial acetic acid. The reactor was cooled and assembled in the hood with nitrogen and hydrogen sources. The reaction mixture was bubbled with dry nitrogen, to replace the air in the reaction mixture and in the reactor, through the inlet with a tubing reaching nearly to the bottom of the reactor. The nitrogen was turned off and the reactor was pressurized with hydrogen through the other inlet. Under a hydrogen pressure of 725 psig, the reaction mixture was heated to 100° C. and stirred at this temperature for 5 days. Hydrogen was refilled whenever it was necessary. After cooling down to room temperature, the excess hydrogen was vented from the reactor and the reactor was opened. The mixture was filtered by suction to remove the solid Pd/C catalyst. The filtrate was rotavapped to remove the acetic acid and water. The crude product was washed with ether and recrystallized from a dilute aqueous solution. A pure product was obtained after two recrystallizations. Elemental analysis: Calculated for $C_{12}H_{17}NO_2$: C:68.87; H:9.15; N:6.69. Found: C:68.85; H:9.12; N:6.75.

6. Synthesis of 3-Diamantanone

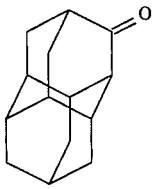

3-Diamantanone can be synthesized from diamantane by the method described by Courtney et. al., J. Chem. Soc. Perkin Trans. I 1972, 2691–6 employing concentrated sulfuric acid at 75° C. for four hours to convert diamantane to 3-diamantanone at 54% yield. Gund et al., J. Org. Chem. 1974, 39(20), 2987–94, used the same procedure to obtain the ketone from diamantane. See also, Gund et al., Tetrahedron Letter 1970, 4875–8. Janku et al., Z. Chem. 1981, 21, 67–68 described a similar procedure giving 86% yield of 3-diamantanone. We have used a modification of the method of Janku et al. by reacting diamantane with concentrated sulfuric acid (about 5 ml conc. $H_2SO_4$/g diamantane) at 80° C. for 48–96 hours. The time required depends on the agitation and the mixing of the subliming diamantane with the acid solution. The progress of the reaction can be monitored by taking small aliquots from the reaction mixture and performing standard aqueous work-up procedure to give solutions analyzed by gas chromatography method. At the end of the reaction, the solution is cooled and any small amount of unreacted diamantane solid removed by filtration. The resulting acid solution is poured into ice. The crude product was collected by filtration, washed thoroughly with water, and dried. The slight discoloration of the crude product can be removed by dissolving the product in hot hexanes and filtering through a solid absorbant such as silica gel or alumina. The crude product, often consisting of over 97% 3-diamantanone, can be further purified by standard techniques to give 3-diamantanone with purities of 99.5–99.9% based on gas chromatography analysis. One method involves recrystallization using ethyl acetate or hexanes. Another involves liquid chromatography on silica gel using a gradient of 0–10% acetone in hexanes as the eluent. The purified product tested has a melting point of 248.8°–250.8° C. It shows the expected proton and carbon 13 NMR spectra. GC analysis showed less than 0.7% impurities. The yields of 3-diamantanone range from 83–90% using our method for reactions employing about 30 to 450 g of diamantane.

7. Synthesis of 2,4-Adamantanedione

2,4-Adamantanedione has been synthesized by oxidation of adamantanone with $CrO_3$ and isolating it from the resulting complex mixture at a low yield (Gilbert, Synthetic Communication 1985, 15(1), 53–56). Alternatively, adamantane-2,4-dione was made by a three-step procedure which requires a chromatographic separation at one of the steps (Faulkner et al., J. Chem. Soc. (C), 1971, 3606–10; Henkel and Spector, J. Org. Chem. 1983, 48, 3657–61). An improved synthesis of this dione, which does not require a chromatographic separation was described in allowed U.S. application Ser. No. 07/946,706 filed Sep. 18, 1992, which is herein incorporated by references in its entirety as if fully set forth.

8. Synthesis of 4(e)-Hydroxy-2-Adamantanone Ethylene Glycol Ketal

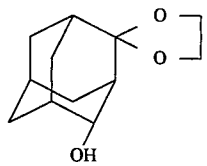

This compound was synthesized using the procedure described by Henkel and Spector, J. Org. Chem. 1983, 48, 3657–61. It can also be made using the improved synthesis of its hydroxy precursor described in U.S. application Ser. No. 07/946,706 filed Sep. 18, 1992.

The following diamondoid compounds were dissolved in ethanol at a concentration of 20 mg/ml:
Compound
1. 1,3,5,7-tetrahydroxyadamantane
2. 1,3-dihydroxy-5,7-dimethyladamantane
3. N-3-diamantyl-N,N,N',N',N'-pentamethyl propane-1,3-bis ammonium diiodide
4. N-2-adamantyl-N,N,N',N',N'-pentamethyl ethane-1,2-bis ammonium diiodide
5. N-2-adamantyl glycine
6. 3-diamantanone
7. 2,4-adamantanedione
8. 4(e)-hydroxy-2-adamantanone ethylene glycol ketal Cell Line The MT-2 cell line, a human T-cell leukemia line derived from isolated cord blood lymphocytes cocultured with cells from patients with adult T-cell leukemia, was obtained from AIDS Research and Reference Reagent Programme of the NIAID, NIH (cat. no. 237, NIH, Bethesda, Md.). The MT-2 cell line can be successfully used as targets for HIV-1 infection and requires only 4 to 5 days for complete cytopathic effect (CPE). (Montefiori et al., J. Clin. Microbiol 1988, 26, 231–235; Pauwels et al., J. Virol. Meth. 1988, 20, 309–321; Harada et al., Science 1985, 229, 563–6)

The MT-2 cell line was grown and maintained in RPMI 1640 containing 10% fetal calf serum and antibiotics.

Viruses

MN/H9 (HIV-$1_{MN}$) (cat. no. 317) was obtained from the AIDS repository.

The AZT resistant strain (AZTR) of HIV-1 (cat. no. 629) which was isolated from an AIDS patient and developed by Douglas Richman was also obtained from the AIDS repository. (Larder et al., Science, 1989, 243, 1731–1734)

VP6 was a primary HIV isolate obtained by culturing PBMC from a patient with full blown AIDS and kaposi sarcoma, with normal phytohemagglutinin (PHA) stimulated PBMC.

Virus-infected cells were grown in RPMI 1640 medium, supplemented with 10% fetal bovine serum and 10% interleukin-2. Cell-free supernatant fluid was collected when the cultures showed peak infectivity titer and was used as the virus stock. AZTR and VP6 stocks were grown in MT-2 cells. MN was grown in H9 cells. The cell free virus stocks were prepared as per the standard (HIV Research Protocol). The virus stocks were titrated by tissue culture infective dose (50%) $TCID_{50}$ by inoculating tissue culture and determining observable effects in 50% of the cultures per Reed and Muench, Amer. J. Hyg., 1938, 27, 493–7.

EXAMPLE 1

Cytotoxicity Assay

An effective anti-viral drug must be non-toxic to cells. Any antiviral assays must first confirm the testing candidate is not cytotoxic to the cells used in the assay. Because viruses use cellular machinery for replication, cytotoxic compounds would inhibit viruses by definition. The microliter cytotoxicity assay used was based on the ability of living cells to reduce the tetrazolium salt MTT (3[4,5-dimethylthiazol-2-yl]-2,5-diphenyltetrazolium bromide) and form a blue product (Tada, H, et al., J. Immuno. Meth. 1986 93, 157–165; Carmichael et al., Cancer Research 1987, 47, 936). Precisely, when the MT-2 cells were in log phase and $2 \times 10^4$ cells were distributed in each well along with separate 100 μl aliquots of diluted test compounds. The test compounds were soluble in ethyl alcohol (EtOH). Ethanol and medium were incubated in some wells with the cells as an ethanol control. A cell control was also included (wells containing only cells and medium). The plates were incubated for 5 days at 37° C. in 5% $CO_2$ and humidified conditions. Cell viability was determined in each well by the MTT assay. The details of the assay are summarized in FIG. 1. The $OD_{570}$ (optical density at 570 nm) of cells without test compound was taken as 0% killing and was compared to the $OD_{570}$ of cells with test compound. The toxicity profile for different compounds was then scored. The results are shown in Table 1. In the MTT dye reduction assay toxicity was indicated as yellow in the wells, with blue color indicating the compound was non-toxic.

TABLE 1

| Compound | Solubility | | Toxicity (µg/ml) | | | |
|---|---|---|---|---|---|---|
| | $H_2O$ | EtOH | 500 | 50 | 5 | .5 |
| 1 | + | + | − | − | − | − |
| 2 | − | + | + | − | − | − |
| 3 | + | + | + | − | − | − |
| 4 | + | + | − | − | − | − |
| 5 | + | + | − | − | − | − |
| 6 | + | + | + | − | − | − |
| 7 | + | + | − | − | − | − |
| 8 | + | + | + | − | − | − |

− = non-toxic

The toxicity of the compounds was tested at concentrations up to 500 µg/ml. The results in Table 1 show that the compounds were non-toxic at most therapeutically useful concentrations.

EXAMPLE 2

Anti-HIV Assay

Stock solutions of the different test compounds were appropriately diluted to give final concentration of 2.5, 5, 10 and 20 µg/ml in RPMI medium when 100 µl of each dilution was added to three replicate wells in 96-well flatbottomed microliter plates. MT-2 cells were inoculated with 100 TCID 50 of HIV-1/MN, the AZT resistant isolate or the VP6 isolate in Ti-25 flasks and incubated for two hours at 37° C. The cells were then washed to remove any remaining free virus, and 2×10⁴ cells were distributed to each of the wells. In cell control only, uninfected cells were distributed. Virus control wells had only infected cells and medium. The plates were incubated at 37° C. for 5 days. HIV-1 induced syncytia were observed after 48 hours. Pictures were taken, shown in FIG. 2 and FIG. 3. After day 5, when maximum CPE was observed in virus control wells, the MTT assay was performed and percent protection was calculated for each drug, applying the following formula:

$$\frac{(OD_T)HIV - (OD_C)HIV}{(OD_C)mock - (OD_C)HIV} \text{ (expressed in \%)}$$

in which $(OD_T)HIV$ is the optical density measured in HIV-infected cells treated with a given concentration of the test compound; $(OD_C)HIV$ is the optical density measured for the control untreated HIV-infected cells. $(OD_C)$mock is the optical density measured for the control untreated mock infected cells. All O.D. values were determined at 570 nm. For pretreatment experiments, cells were incubated with test compounds for 1 hour at 37° C. prior to infection with the virus. After the adsorption of virus, these cells were washed, the wells replenished with medium containing test compound. The remaining part of the assay was continued as above. Pictures were taken on day 5 (See FIG. 2). The percent protection from these tests was plotted and is depicted in FIG. 4.

EXAMPLE 3

Virus Neutralization Assay

50 µl of cell free virus (100 TCID50) were mixed with 50 µl of different concentrations of the test compounds. Virus-compound mixtures were incubated at 37° C. for 1 hour, then added to the wells of a 96-well flat-bottomed microtiter plate containing 6×10⁴ MT-2 cells/well. The plates were incubated at 37° C. in 5% $CO_2$ humidified atmosphere for 5 days. MTT reduction assay was performed on day 5. The neutralization pattern was assessed and the results summarized in Table 2.

TABLE 2

| | MN | | Clinical Isolate | | | | |
|---|---|---|---|---|---|---|---|
| | | | | AZTR | VP6 | AZTR | VP6 |
| Compound | Post-Infection | Neutral-ization | Pre-Infection | Post-Infection | Post-Infection | Pre-Infection | Pre-Infection |
| 1 | +++ | ++ | ++ | − | − | − | − |
| 2 | +++ | +/− | +/− | − | − | − | − |
| 3 | +++ | +++ | ++ | − | − | − | − |
| 4 (ND) | | | | | | | |
| 5 | +++ | − | − | − | − | − | − |
| 6 | ++++ | +++ | +++ | ++ | ++ | ++ | ++ |
| 7 | − | ++ | ++ | − | − | ++ | ++ |
| 8 | − | ++ | ++ | − | − | − | − |

++++ = greatest neutralization (ND) = not done
−−− = no neutralization

A rating of ++++ or +++ indicates significant and reproducible inhibition of cytopathic effect; + indicates noticeable but minimal protection; −−− or − means no protective effect was observed. A rating of − indicates no protection was observed but some changes in the cell culture occurred. Because assays in different columns were rated and compared with control for that column, ratings under different columns should not be compared quantitatively. Since the clinical isolates AZTR and VP6 do not induce as severe a cytopathic effect as HIV-1$_{MN}$ does, it is unlikely that any compounds will be rated higher than ++ against the clinical isolates.

As measured by the assays, compounds 1, 2, 3 and 6 were found to be effective in both pre-infection and post-infection assays against the HIV-1$_{MN}$ strain. Compounds 1, 2, 3, 6, 7 and 8 were effective in pre-infection and neutralization assays and compounds 1, 2, 3, 5 and 6 were effective in post-infection assays.

Compound 6 was found to completely inhibit HIV-1$_{MN}$ induced syncytia at a very low concentration (10 µg/ml; shown in FIG. 2). Compound 7 was found to substantially eliminate syncytia formation. Furthermore, compound 6 was found to be effective in both pre-treatment and in post-infection while compound 7 inhibited viral cytopathic effect in pretreatment of the MN virus strain.

Importantly, compound 6 inhibited virus replication with AZT resistant strains and VP6 clinical isolates as well in both pre- and post-infection assays, while compound 7 inhibited CPE of HIV in pre-infection assays on both AZT resistant and VP6 clinical isolates.

The percent protection by different compounds which inhibited CPE is illustrated in FIG. 4. It is clear that some of the derivatives inhibited HIV-1 induced CPE by up to 80%.

We have shown that diamondoid derivatives inhibit HIV-1 induced CPE in living cells as well as syncytia at significant levels. For compound 7, pretreatment is more effective than post-infection treatment. While not wishing to be bound by any one theory, this suggests that compound 7 may act early in the viral life cycle to inhibit viral entry into cells inhibiting initiation of infection or other steps. Compound 6 is active in both pre- and post-infection and in neutralization assays, suggesting that it is acting in the later stages of the viral life cycle. No compound currently approved for use in HIV patients works at the late stages of the virus life cycle. Furthermore, compounds 6 and 7 were shown to inhibit clinical isolates and AZT resistant isolates. It is also noted that compounds 6, 7 and 8 are diamondoid ketones and derivatives, for which no known pharmacological activity has been reported. Compounds 3, 4 and 5 are derived from ketones as described in the synthesis above. Because some related compounds have not shown activity against HIV-1 in the same assays, it is concluded that effective compounds derive their activity from a particular arrangement of polar functional groups on the diamondoid framework.

Other compounds tested were N-(2-adamantyl)-N,N,N',N',N'-pentamethyl-propane-1,3-bis ammonium diodide, adamantane-2,6-dione, 5-hydroxy-2-adamantanone, diamantane-3,5-dione and 2-adamantanone. These compounds were ineffective under the rigorous testing conditions used in these examples, e.g., high virus load. It was therefore concluded that under these rigorous conditions when the compound of formula I has more than one polar group, a first polar group is separated from the closest second polar group by no more than two carbon atoms of the diamondoid compound, counted by the shortest route. With compounds of formula II, ketones with a 1,3 relationship were ineffective under the rigorous testing conditions used in these examples.

We claim:

1. A method of inhibiting a retrovirus which comprises contacting the virus, a virus-infectable cell or a virus-infected cell with a compound of formula I, formula II or combinations thereof:

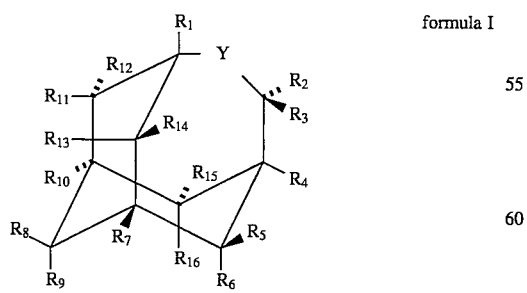

formula I wherein
Y is a bond,
$R_1$, $R_4$, $R_7$ and $R_{10}$ are individually hydrogen, hydroxyl or methyl;
$R_2$, $R_3$, $R_5$, $R_6$, $R_8$, $R_9$, $R_{11}$, $R_{12}$, $R_{13}$, $R_{14}$, $R_{15}$ and $R_{16}$ are individually hydroxyl double bonded oxygen

an amino acid, a secondary amine, a tertiary amine or hydrogen;
except $R_1$–$R_{16}$ are not all hydrogen and at least one of $R_1$–$R_{16}$ is a polar group, or

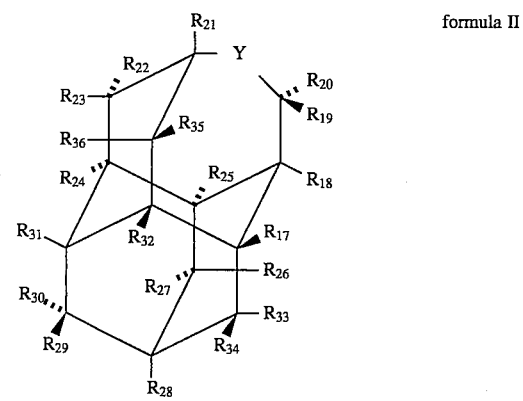

formula II wherein
Y is a bond,
$R_{17}$, $R_{18}$, $R_{21}$, $R_{24}4$ $R_{25}$, $R_{28}$, $R_{31}$ and $R_{32}$ are hydrogen;
$R_{19}$, $R_{20}$, $R_{22}$, $R_{23}$, $R_{26}$, $R_{27}$, $R_{29}$, $R_{30}$, $R_{33}$, $R_{34}$, $R_{35}$ and $R_{36}$ are individually hydrogen, double-bonded oxygen,

formula B

formula C wherein
$R_c$ is methyl
$R_d$ is methyl,
$R_e$ is $(CH_2)_n \overset{+}{N}R'R''R'''(CH_3)_3(X^-)$, n=2 or 3, or lower alkyl of 1 to 8 carbons,
$R_f$ is methyl
X is a counterion except that $R_{17}$–$R_{36}$ are not all hydrogen and at least one of $R_{17}$–$R_{36}$ is a polar group
with the proviso that the compounds of formula I have one, two or four polar groups and when the compound of formula I has more than one polar group, the polar groups are present in a 1,3; 2,4; or 1,3,5,7 relationship; and the compounds of formula II have one polar group, wherein the compound is selected from the group consisting of diamondoid alcohols, diamondoid polyols, diamondoid amino acids, diamondoid quaternary ammonium salts and diamondoid ketones.

2. The method of claim 1 wherein the compound of formula I is selected from the group consisting of 1,3,5,7-adamantane tetraol;

1,3-dihydroxy-5,7-dimethyladamantane;

N-2-adamantyl glycine;

2,4-adamantanedione;

4(e)-hydroxy-2-adamantanone ethylene glycol ketal and combinations thereof.

3. The method of claim 1 wherein the compound of formula II is selected from the group consisting of N-3-diamantyl-N,N,N',N',N'-pentamethyl-propane-1,3-bis ammonium diiodide and 3-diamantanone.

4. The method of claim 1 wherein the compound is selected from the group consisting of 2,4-adamantanedione, 3-diamantanone and 4(e)-hydroxy-2-adamantanone ethylene glycol ketal.

5. The method of claim 1 wherein the compound is 2,4-adamantanedione.

6. The method of claim 1 wherein the compound is 3-diamantanone.

7. The method of claim 1 wherein the compound is 4(e)-hydroxy-2-adamantanone ethylene glycol ketal.

8. The method of claim 1 wherein the retrovirus is HIV-1.

9. A method for treating humans or animals suffering from a retrovital infection comprising administering to said human or animal a retrovital inhibiting amount of a compound of formula I or formula II as described in claim 1.

10. The method of claim 9 wherein the compound of formula I is selected from the group consisting of 1,3,5,7-adamantane tetraol;

1,3-dihydroxy-5,7-dimethyladamantane;

N-2-adamantyl glycine;

2,4-adamantanedione;

4(e)-hydroxy-2-adamantanone ethylene glycol ketal and combinations thereof.

11. The method of claim 9 wherein the compound of formula II is selected from the group consisting of N-3-diamantyl-N,N,N',N',N'-pentamethyl-propane-1,3-bis ammonium diiodide and 3-diamantanone.

12. A kit for screening retrovirus comprising a compound of formula I or formula II as described in claim 1.

13. The kit of claim 12 wherein the compound is selected from the group consisting of 1,3,5,7-adamantane tetraol;

1,3-dihydroxy-5,7-dimethyladamantane;

N-3-diamantyl-N,N,N',N',N'-pentamethyl propane-1,3-bis ammonium diiodide;

N-2-adamantyl glycine;

3-diamantanone;

2,4-adamantanedione; and

4(e)-hydroxy-2-adamantanone ethylene glycol ketal.

* * * * *